(12) United States Patent
Tamez et al.

(10) Patent No.: US 10,568,997 B2
(45) Date of Patent: Feb. 25, 2020

(54) IMPLANT CONNECTOR

(71) Applicant: HeartWare, Inc., Miami Lakes, FL (US)

(72) Inventors: Daniel Tamez, Plantation, FL (US); Virote Indravudh, Santa Clarita, CA (US); Richard A. Marquis, Miami, FL (US); Charles R. Shambaugh, Coral Gables, FL (US); Jeffrey A. Larose, Sunrise, FL (US)

(73) Assignee: HeartWare, Inc., Miami Lakes, FL (US)

( * ) Notice: Subject to any disclaimer, the term of this patent is extended or adjusted under 35 U.S.C. 154(b) by 293 days.

(21) Appl. No.: 15/667,238

(22) Filed: Aug. 2, 2017

(65) Prior Publication Data

US 2017/0326280 A1 Nov. 16, 2017

Related U.S. Application Data

(62) Division of application No. 11/298,410, filed on Dec. 8, 2005, now Pat. No. 9,744,279.

(51) Int. Cl.
*A61M 1/10* (2006.01)
*A61M 1/12* (2006.01)

(52) U.S. Cl.
CPC .......... *A61M 1/10* (2013.01); *A61M 1/1008* (2014.02); *A61M 1/122* (2014.02); *A61M 1/101* (2013.01)

(58) Field of Classification Search
CPC .......... A61B 17/7011; A61B 17/7023; A61B 17/7035; A61B 17/7022; A61B 17/7037; A61B 17/7038; A61B 2017/1135; A61M 1/10; A61M 1/122
See application file for complete search history.

(56) References Cited

U.S. PATENT DOCUMENTS

| | | |
|---|---|---|
| 4,790,843 A | 12/1988 | Carpentier et al. |
| 5,084,064 A | 1/1992 | Barak et al. |
| 5,354,331 A | 11/1994 | Schachar |
| 5,486,174 A | 1/1996 | Fournet-Fayard et al. |
| 5,504,978 A | 4/1996 | Meyer |
| 5,562,688 A | 10/1996 | Riza |

(Continued)

FOREIGN PATENT DOCUMENTS

| | | |
|---|---|---|
| KR | 2019970055361 | 10/1997 |
| WO | 200047270 A2 | 8/2000 |

OTHER PUBLICATIONS

Chinese Office Action dated Feb. 23, 2016, in Indian Patent Application No. 4926/DELNP/2008.

(Continued)

*Primary Examiner* — Alexander J Orkin
(74) *Attorney, Agent, or Firm* — Christopher & Weisberg, P.A.

(57) ABSTRACT

A connector for connecting an implant device to tissue of a person's body. The connector including a frame having first and second arms. The first and second arms define an opening, where at least a portion of the implant device is inserted through the opening. After insertion, an additional securing member is connected to the frame. The securing member is adapted to receive at least one suture to secure the frame to the tissue. The connector includes an adjuster that is movably connected to the first and second arms, where the adjuster is operable to cause the first and second arms to move toward each other and engage the implant device.

10 Claims, 5 Drawing Sheets

(56) References Cited

U.S. PATENT DOCUMENTS

| | | |
|---|---|---|
| 5,824,069 A | 10/1998 | Lemole |
| 5,938,663 A | 8/1999 | Petreto |
| 6,143,025 A | 11/2000 | Stobie et al. |
| 6,319,231 B1 | 11/2001 | Andrulitis |
| 6,458,163 B1 | 1/2002 | Slemker et al. |
| 6,551,270 B1 | 4/2003 | Bimbo et al. |
| 6,732,501 B2 | 5/2004 | Yu et al. |
| 2002/0042605 A1 | 4/2002 | Castaneda et al. |
| 2002/0058994 A1 | 5/2002 | Hill et al. |
| 2002/0095210 A1 | 7/2002 | Finnegan et al. |
| 2003/0009238 A1 | 1/2003 | Whayne |
| 2003/0023255 A1 | 1/2003 | Miles et al. |
| 2003/0023302 A1 | 1/2003 | Moe et al. |
| 2003/0040753 A1 | 2/2003 | Daum et al. |
| 2004/0007515 A1 | 1/2004 | Geyer |
| 2004/0015232 A1 | 1/2004 | Shu et al. |
| 2004/0026224 A1 | 1/2004 | Yu et al. |
| 2004/0024285 A1 | 2/2004 | Muckter |
| 2004/0030381 A1 | 2/2004 | Shu |
| 2004/0122514 A1 | 6/2004 | Fogarty et al. |
| 2004/0167376 A1 | 8/2004 | Peters et al. |
| 2004/0171905 A1 | 9/2004 | Yu et al. |
| 2004/0210305 A1 | 10/2004 | Shu et al. |
| 2005/0010238 A1 | 1/2005 | Potter et al. |
| 2005/0043685 A1 | 2/2005 | Schinkel-Fleitmann |
| 2006/0074271 A1 | 4/2006 | Cotter |
| 2012/0010455 A1 | 1/2012 | Reichenbach et al. |

OTHER PUBLICATIONS

Official Action dated Jan. 31, 2013 in Korean Patent Application No. 10-2008-7016102.

Supplementary European Search Report issued by the European Patent Office dated Apr. 15, 2013 in connection with European Patent Application No. 06845159.0.

IMPLANT CONNECTOR

CROSS-REFERENCE TO RELATED APPLICATIONS

This application is a divisional of U.S. patent application Ser. No. 11/298,410, filed Dec. 8, 2005, now U.S. Pat. No. 9,744,279, the entirety of all of which are incorporated herein by reference

BACKGROUND

Thousands of heart patients who suffer from severe ventricular heart failure could benefit from cardiac transplantation. However, because of a shortage of donor hearts, most of these patients face a shortened life span characterized by frequent hospitalizations, severe physical disability, and death from congestive failure or cardiogenic shock.

One medical device developed to aid these heart patients is a heart pump such as a ventricular assist device ("VAD") which enables heart patients to return to prolonged and productive lives. Heart pumps are typically connected to the left ventricle of the heart. One end of a tube such as a graft is connected to the heart pump and the other end is connected to the ascending Aorta or the descending Aorta. Once connected, the heart pump pumps blood from the left ventricle to the ascending or descending Aorta to improve blood flow.

Conventional heart pump implant methods utilize connectors called sewing rings which are attached to the myocardium of the heart using sutures. A separate surgical tool is then used to cut a hole centered in the myocardium through the sewing ring. A shaft extending from the heart pump is inserted through the hole and into the left ventricle. The sewing ring is used to clamp and hold the heart pump in position on the heart.

To prevent life threatening hemorrhaging and other complications, a sewing ring must hold the heart pump securely in position. Furthermore, the seal between the sewing ring and the heart pump must be sufficiently tight to prevent blood loss from the heart.

Accordingly, there is a need for an improved connector which securely holds a heart pump in place and which seals the connection between the connector and the heart pump to minimize patient complications from heart pump implant surgery.

SUMMARY

The present invention is directed to a surgical connector and more specifically, to an implant connector which secures and seals an implant device to a patient's heart.

In an embodiment, a connector for connecting an implant device to tissue of a person's body is provided where the connector includes a frame and a securing member. The frame includes first and second arms, where the first and second arms define an opening. The opening is sized and shaped to receive at least a portion of the implant device to secure the device in place. The connector includes a securing member connected to the frame. The securing member is adapted to receive at least one suture to secure the frame to the tissue. The connector also includes an adjuster movably connected to the first and second arms, where the adjuster is operable to cause the first and second arms to move toward each other and engage the implant device.

In an embodiment, the connector includes an additional securing member positioned between the securing member and the frame. The additional securing member is at least partially enclosed and supported by the securing member. In an embodiment, the securing member includes a lip which substantially covers the additional securing member. The additional securing member provides cushioning or padding to minimize discomfort and stress on the heart.

In an embodiment, at least one of the securing members includes felt. In another embodiment, at least one of the securing members includes polyester. It should be appreciated that the securing members may include the same or different materials.

In another embodiment, the connector includes a sealer that is removably connected to the frame. The sealer may be an o-ring, gasket or any other suitable type of sealer or sealing device.

In an embodiment, the adjuster is a screw which is threadingly engaged with at least one of the first and second arms.

In an embodiment, the connector includes a pin that is frictionally connected to one of the first and second arms to substantially minimize lateral movement of the adjuster. The pin therefore holds the screw in place and helps to prevent the screw from disengaging from the frame.

In an embodiment, the frame defines at least one opening sized to accept at least one suture for securing the frame to the securing member. The frame may define one or a plurality of openings.

In another embodiment, an implant connector is provided which includes a frame including first and second cantilevered arms. The first and second cantilevered arms define an opening, where at least a portion of the implant device is inserted through the opening. The connector includes a securing member connected to the frame. The securing member is adapted to receive at least one suture to secure the frame to the tissue. The connector further includes an additional securing member positioned adjacent to the securing member. The additional securing member is at least partially enclosed by the securing member. The connector includes an adjuster movingly connected to the first and second arms, where the adjuster is operable to cause at least one of the first and second arms to move toward the other of the first and second arms and engage the implant device.

In an embodiment, the securing member includes a lip which substantially covers the additional securing member. The lip defines a pocket which is sized to receive and substantially enclose the additional securing member.

In an embodiment, the connector includes a sealer that is removably connected to the frame. The sealer helps to seal the area between the frame and the implant device. In one embodiment, the sealer includes an o-ring.

In an embodiment, the adjuster is a screw which is threadingly engaged with at least one of the first and second cantilevered arms.

In another embodiment, the connector includes a pin which is frictionally connected to one of the first and second cantilevered arms to substantially minimize lateral movement of the adjuster. The pin may be any suitable size and shape. In an embodiment, the pin at least partially engages a groove defined by the adjuster.

In a further embodiment, an implant connector is provided which is used to connect an implant device to tissue of a person's body. The implant device includes a frame including first and second arms. The first and second arms define an opening. The implant connector also includes a positioner movably connected to the frame and positioned in the opening defined by the first and second arms. The positioner defines an opening, where at least a portion of the implant device is secured in the opening and the positioner is moved to adjust the position of the implant device. The implant connector also includes a securing member connected to the frame. The securing member is adapted to receive at least one suture to secure the frame to the tissue. An adjuster is movably connected to the first and second arms. The adjuster is operable to cause the first and second arms to move toward each other and engage the implant device.

In an embodiment, the positioner is made with a pliable material.

It is therefore an advantage of the present invention to provide an implant connector which is easy to implant, use and adjust.

Another advantage of the present invention is to provide an implant connector which creates at least three points of contact between the connector and the implant device.

A further advantage of the present invention is to provide an implant connector which utilizes cantilevered arms to significantly enhance the seal between the connector and an implant device.

Another advantage of the present invention is to provide an implant connector which includes a positioner that enables a user to adjust the position of a heart pump secured in the implant connector.

Other objects, features and advantages of the invention will be apparent from the following detailed disclosure, taken in conjunction with the accompanying sheets of drawings, wherein like numerals refer to like parts, elements, components, steps and processes.

DETAILED DESCRIPTION

Figure 1:
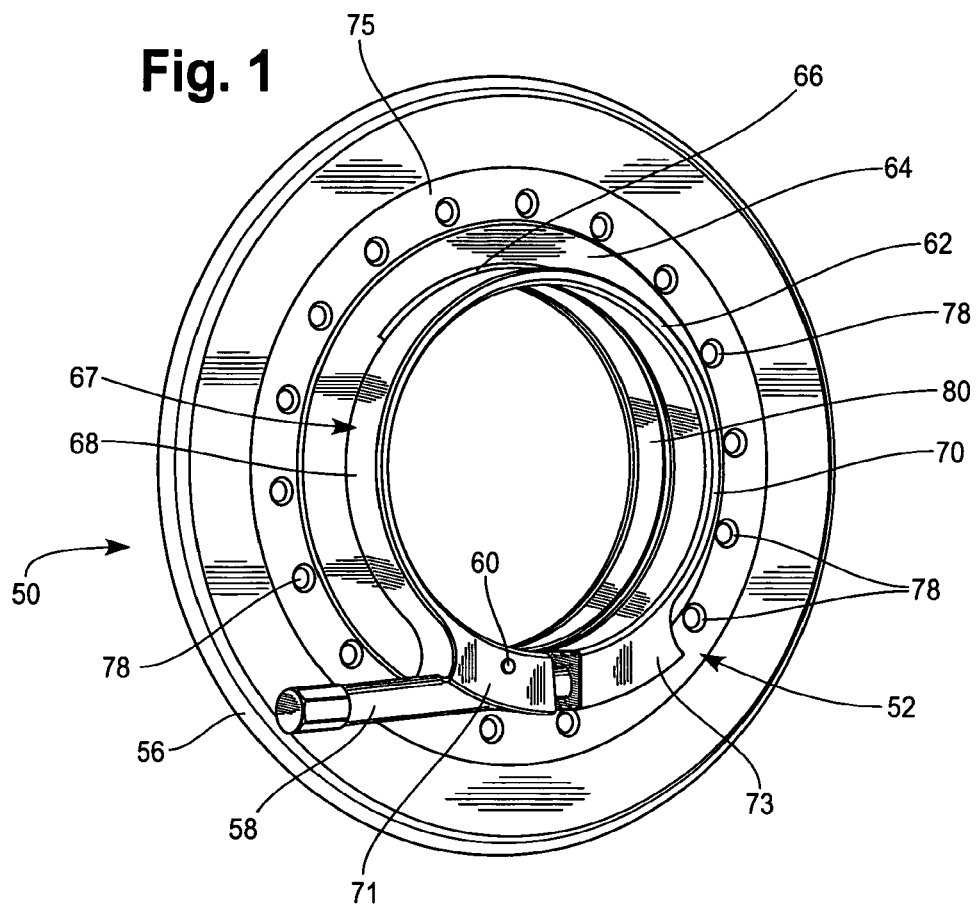
FIG. 1 is a perspective view of one embodiment of the implant connector of the present invention.

Referring to FIG. 1, one embodiment of an implant connector or ventricular connector 50 of the present invention is illustrated where the implant connector enables an implant device such as a heart pump to be efficiently, securely and safely attached to a heart.

In one embodiment, the implant connector 50 includes a substantially circular or round frame 52, a first member or first ring 54 and a second member or second ring 56. The frame 52 includes a first planar member or wall 62 which is transverse to and extends generally upwardly or away from a second planar member or flange 64. The first planar member 62 has a generally circular shape and a diameter determined based on the diameter of the inflow tube connected to a heart pump. It should be appreciated that the size and shape of the first planar member varies based on the size and shape of the inflow tube and the heart pump. In this regard, the first planar member or wall 62 may be any suitable size and shape. The flange 64 is substantially flat and extends outwardly away from the outside surface of the wall 62.

Figure 4:
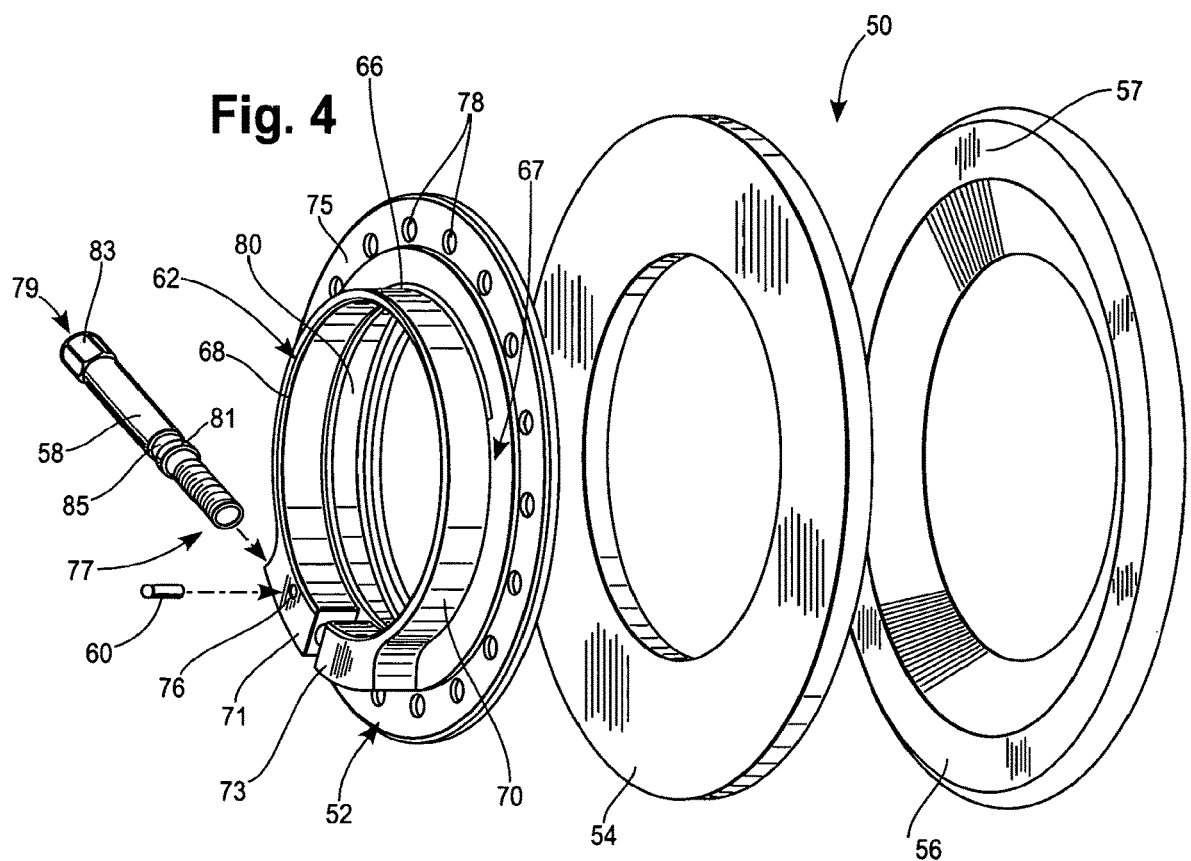
FIG. 4 is an exploded perspective view of the implant connector of FIG. 1.
Figure 5:
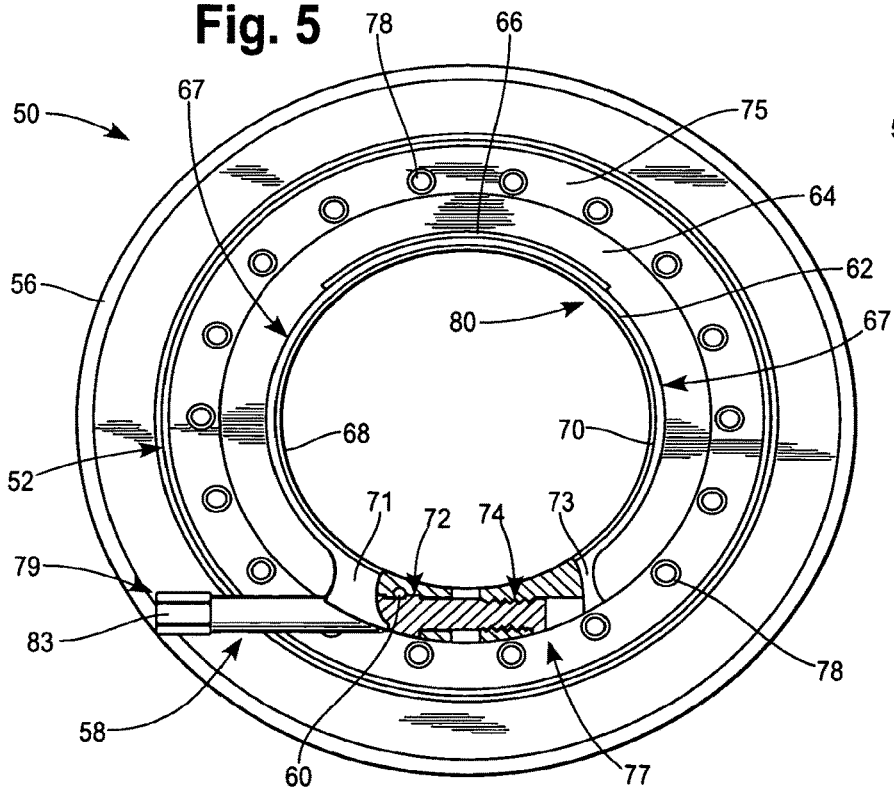
FIG. 5 is a front view of the implant connector of FIG. 1 where a portion of the connector is shown cut away.
Figure 6:
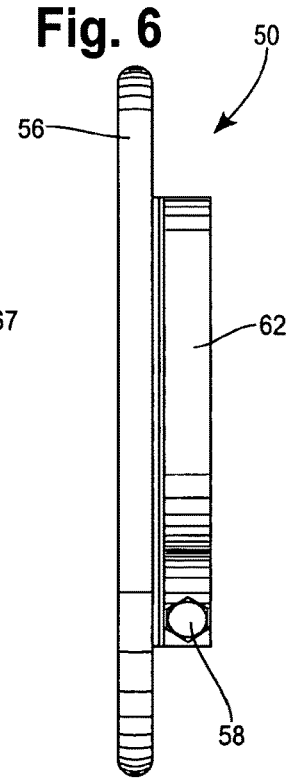
FIG. 6 is a side view of the implant connector of FIG. 1.

In one embodiment, the wall 62 is attached to a designated portion or length of the inside edge of the flange 64 as shown by attachment wall 66 in FIG. 1 to form or define two cantilevered extenders or arms 68 and 70. As shown in FIGS. 1 and 4 the attachment wall 66 is integrally formed with the wall 62 and flange 64. In another embodiment, the attachment wall 66 is a separate component which is connected to the wall 62 and the flange 64 using any suitable connection or attachment method.

In the illustrated embodiment, the first arm 68 extends substantially along the inside edge or surface of a first side of the flange 64 and ends at a point substantially opposite to the attachment wall 66. Similarly, the second arm 70 extends substantially along the inside edge or surface of an opposite or second side of the flange 64 and ends at a point adjacent to the end of the first arm 68 and substantially opposite to the attachment wall 66. As illustrated, the first and second arms 68 and 70 are in substantially the same plane. As shown in FIGS. 1 and 4, the first and second arms are cantilevered or are supported at one end (i.e., the end adjacent to the attachment wall 66) and carry a load at the other end or along its length. As discussed below, the first and second arms 68 and 70 can move inwardly, or towards each other, because the arms are cantilevered or not fixed or supported at one end.

The non-fixed or non-supported ends of the first and second arms 68 and 70 each form or define integral housings. The first arm 68 forms or defines a generally rectangular shaped housing 71. Housing 71 defines a first channel or opening 72. The first channel 72 is generally cylindrically shaped and includes a substantially smooth inside surface. The first channel is also sized to receive at least a portion of the adjuster or tightening screw 58. The second arm 70 forms or defines a generally rectangular shaped housing 73, which defines a second channel or opening 74. The second channel 74 is generally cylindrically shaped and sized to receive at least a portion of screw 58. The inside surface of the second channel 74 includes a plurality of threads to enable the screw 58 to threadingly engage the second channel. In one embodiment, the first and second channels 72 and 74 are in substantially the same plane. This configuration enables the screw 58 to remain in substantially the same plane to minimize the screw from binding up, bending and/or breaking as screw 58 is inserted through channel 72 into engagement with channel 74.

Screw 58 causes cantilevered first and second arms 68 and 70 to move towards each other as the screw is rotated in one of a clockwise or counterclockwise direction. As the first and second arms 68 and 70 move towards each other the clamping force about the perimeter of the shaft extending from the heart pump increases to securely hold the shaft and heart pump in position. In the embodiment shown in FIGS. 1-6, screw 58 is integrally formed and has a generally cylindrical shape and a designated size or length. The length of screw 58 is at least in part determined by the designated distance between housings 72 and 74. In this regard, screw 58 must be long enough to fit through first channel 72 of first housing 71 and extend at least partially into the second channel 74 of housing 73. In one embodiment, screw 58 has a first end 77 and an opposite or second end 79. The first end 77 defines a plurality of threads and is sized to fit into and through channel 74 and at least partially into engagement with the inside surface of channel 72. Intermediate to the first and second ends of screw 58, at least one and preferably, a plurality of threads 81 are defined by the body of the screw. The threads on the screw may be formed to enable the screw to move or rotate in a clockwise or counterclockwise direction. It should be appreciated that any suitable type and number of threads may be defined by the body of the screw.

As shown in FIGS. 1 and 4, the second end 79 of the screw defines a plurality of engagement surfaces 83. The engagement surfaces 83 are configured and shaped to be engaged by a wrench such as a fixed, ratcheting, adjustable or torque wrench or similar tool which may be used to engage and rotate screw 58. It should be appreciated that the engagement surfaces 83 may be any suitable size or shape. Alternatively, the second end 79 of the screw may define a slot such as a flat slot or star-shaped slot for engagement by a suitable screwdriver or similar tool.

Referring now to FIG. 4, the second housing 73 defines a relatively small hole or opening 76 which is sized and shaped to receive retaining member, retainer or pin 60. Pin 60 has a generally cylindrical shape and is inserted at least partially into opening 76 until the pin engages screw 58. The diameter of pin 60 is at least partially larger than the diameter of opening 76 to create a friction fit between the pin and the opening. The friction fit holds the pin 60 in place after the pin is inserted into opening 76. Pin 60 engages the channel or groove 85 defined by screw 58 to maintain the axial or lateral position of the screw and assist in preventing the screw from disengaging from the first and second channels 72 and 74 and possibly falling out onto the floor or into a patient's body. The pin 60 can be any suitable size and shape corresponding to the size and shape of the groove 85 defined by the screw 58.

The bottom surface of flange 64 is connected to outer flange 75. In the illustrated embodiment, the wall 62, the flange 64 and the outer flange 75 are integrally formed to define the frame 52. In another embodiment, at least one of the wall, the flange and the outer flange are manufactured as a separate components and connected together using any suitable connectors or connection method.

The outer or connecting flange 75 has a generally circular shape corresponding to the shapes of the wall 62 and the flange 64. It should be appreciated that the outer flange 75 may be any suitable size and shape. As shown in FIG. 4, the outer flange 75 defines at least one and preferably a plurality of securing holes or openings 78. The openings 78 may be any suitable size or shape. In this embodiment, the openings 78 are spaced evenly (i.e., the same distance from the center of one opening to the center of each adjacent opening) on the outer flange 75. It should be appreciated that the at least one, a plurality or all of the openings may be spaced apart by the same distance, at least one different distance, all different distances or any designated or suitable distance. In the illustrated embodiment, the openings extend from the top surface of the connecting flange to the bottom surface of the connecting flange (i.e., all the way through the flange). The openings 75 help to secure the outer flange, and thereby the implant connector 50, in position as discussed below.

A first securing member or first ring such as circular felt ring 54 is inserted or positioned within a second securing ring 65 member or second ring such as polyester ring 56. The second ring 56 includes a cover or lip 57 which fits over the first ring to cover and at least partially enclose the first ring within the second ring. In the illustrated embodiment, the first ring 54 is a substantially planar member and has an outside diameter which is larger than the outside diameter of the frame as shown in FIG. 4. In this embodiment, the second ring 56 has the same diameter as the first ring. It should be appreciated that the first and second rings may have the same diameter or different diameters. It should also be appreciated that the first and second rings may be any suitable size and shape.

In the illustrated embodiment, the first ring 54 is made of felt. The felt material is a softer material and therefore adds cushioning between the frame and the heart to minimize discomfort. The second ring is made of a more durable material that the first ring such as polyester which is stronger and has more integrity to sufficiently hold one or more sutures. The sutures therefore connect the frame to the second ring to hold the frame, first ring and second ring together. Generally, the sutures are connected between the frame and second ring in the manufacturing process. The frame, first ring and second ring therefore are already secured together (i.e., pre-manufactured) prior to using the implant connector for an implant procedure. It should be appreciated that the frame, first ring and second ring may be secured together at any suitable time. It should also be appreciated that the first ring 54 and the second ring 56 may be made of any suitable material or materials.

Figure 2:
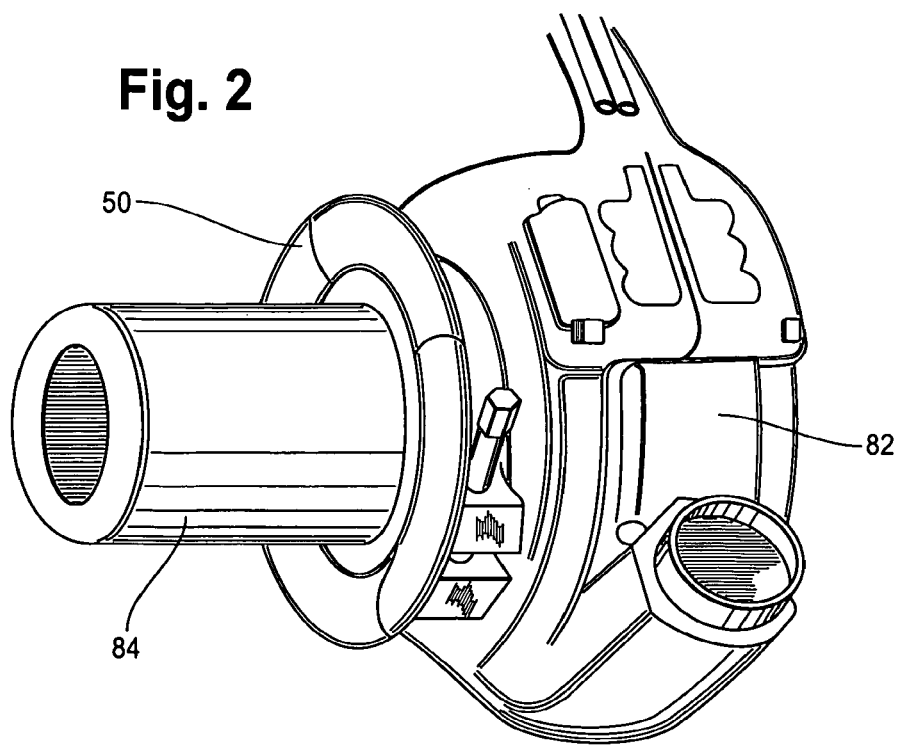
FIG. 2 is a perspective view of the implant connector of FIG. 1 attached to a heart pump.
Figure 3:
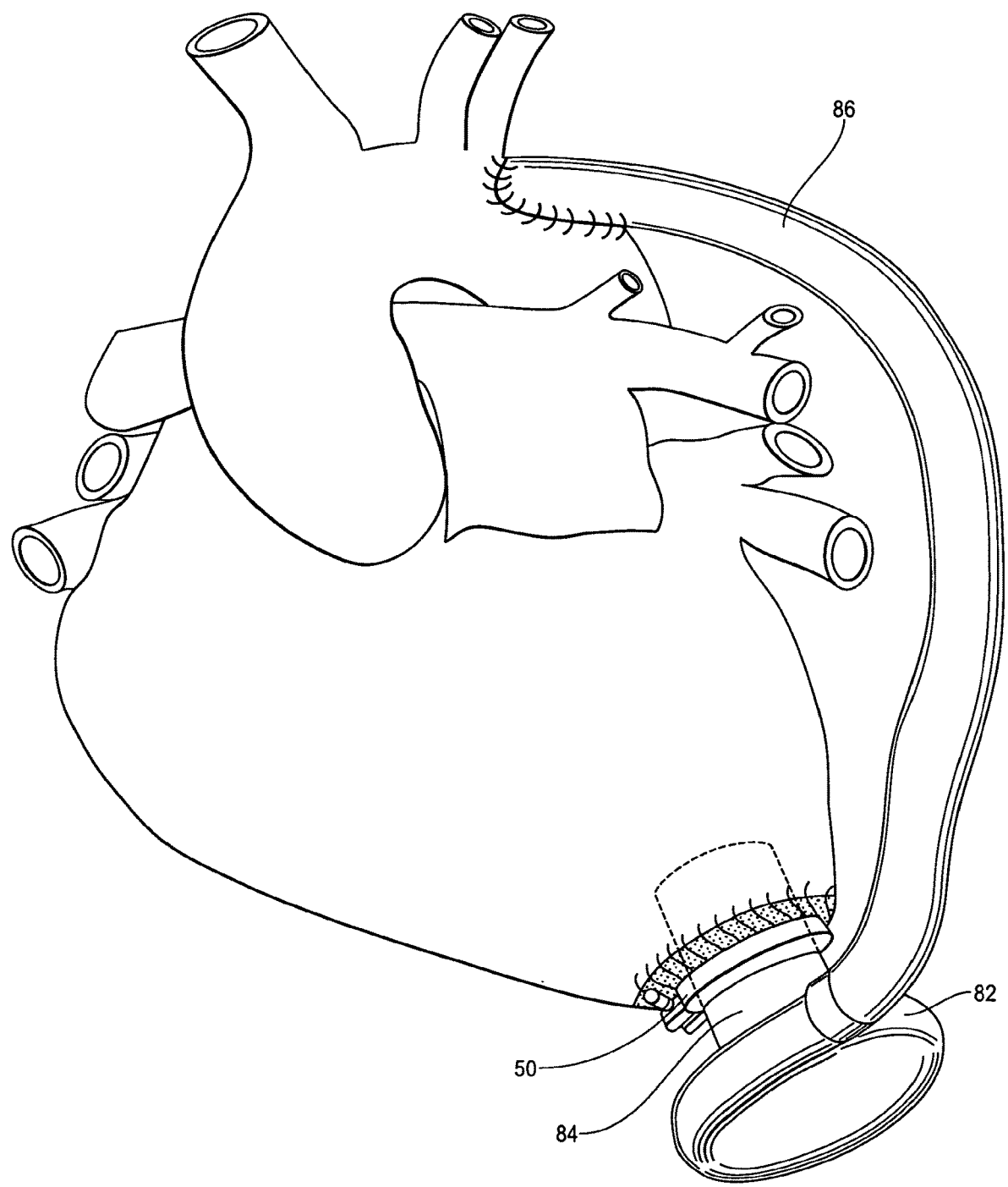
FIG. 3 is a diagrammatic view of the implant connector of FIG. 1 illustrating the connection of the implant connector and a heart pump to a patient's heart.

Referring now to FIGS. 2 and 3, the implant connector 50 is secured to the tissue of a patient to enable an implant device or other suitable device to be securely and safely attached to the tissue. In one example illustrated in FIG. 2, the implant connector 50 is used to secure a heart pump such as a VAD to a patient's heart. The implant connector 50 is first positioned or seated adjacent to one of the ventricles of the heart such as the left ventricle. The implant connector is secured in place by inserting one or more sutures, stitches or the like through the second ring 56 and the tissue forming the left ventricle. As discussed above, at least one suture is inserted through one or more of the attachment openings 78 defined by the frame, the second ring and the tissue of the patient. The sutures are secured to the connector and tissue until the implant connector is firmly secured in position on the left ventricle.

When the implant connector 50 is securely attached to the left ventricle (i.e., the heart), a hole, opening or bore is cut in the heart tissue accessible through the middle or center portion of the implant connector. The hole is cut to gain access to the left ventricle for insertion of at least a portion of an inflow tube attached to the heart pump into the left ventricle. When the hole has been cut, the inflow tube of the heart pump is inserted through the center portion of the implant connector and into the left ventricle as illustrated in FIG. 3. The inflow tube and the heart pump are secured in place by rotating screw 58 using a suitable tool as described above. Rotating the screw causes the cantilevered first and second arms to move or draw closer to each other, which in turn, increases the clamping force on the shaft of the heart pump. The clamping force also compresses the sealer, gasket or o-ring 80 positioned on or removably connected to the inside surface of the frame. The compression of the o-ring between the outside surface of the heart pump shaft and the inside surface of the frame forms a substantially tight seal between the shaft and frame. The tight seal helps to prevent blood loss from the opening or hole in the heart and other complications from arising during the implantation procedure. The tight seal also helps to prevent the shaft and heart pump from moving or rotating after these components are secured to the heart.

To increase the clamping pressure of the implant connector and more specifically, the first and second cantilevered arms of the frame, the screw is rotated in one direction such as a clockwise or counterclockwise direction using a wrench such as a fixed, ratcheting, adjustable or torque wrench. The wrench engages the contact or engagement surfaces 83 located at the end 79 of the screw. Once engaged, the wrench is rotated or turned to correspondingly rotate or turn the screw. Turning the screw causes the threads defined by the first end of the screw to threadingly engage corresponding threads defined by the inside surface of the second channel or opening defined by the second housing 73. As the screw turns, the first arm is pulled toward the second arm thereby decreasing or closing the hole or opening in the center of the frame and increasing the clamping force on the shaft of the heart pump. The screw is turned or rotated until a suitable clamping force and seal is achieved between the frame 52 of the impact connector and the shaft of the heart pump. Once secured, the implant procedure is completed.

As described above and illustrated in FIGS. 1-6, the cantilevered first and second arms of the present implant connector provide at least three points of contact between the frame and the shaft of the heart pump when the arms are tightened to engage the shaft. This is a significant improvement over conventional implant connectors which provide two or less points of contact. The implant connector of the present invention therefore substantially enhances the connection of an implant device such as a heart pump to tissue as well as enhances the seal between the connector and the heart pump. Also, the single adjuster or screw, minimizes the time and effort needed during surgery to tighten the screw to clamp the heart pump in place and/or to adjust the position of the heart pump.

The implant connector of the present invention also enables the inflow tube of the heart pump to be easily adjusted and/or rotated to optimize the position of the VAD or heart pump prior to securing the heart pump in place.

The frame, screw and pin of the implant connector are preferably made with titanium. It should be appreciated however that any suitable metal, metals, combination of metals or any other suitable material or materials may be used to manufacture or make the components of the implant connector.

Referring now to FIGS. 7-10, another embodiment of the implant connector is illustrated where the implant connector 100 includes an implant adjuster movable member or positioner 110 which enables the position of a heart pump to be adjusted after insertion and connection of the heart pump to the implant connector to obtain the optimum position for the heart pump.

Figure 7:
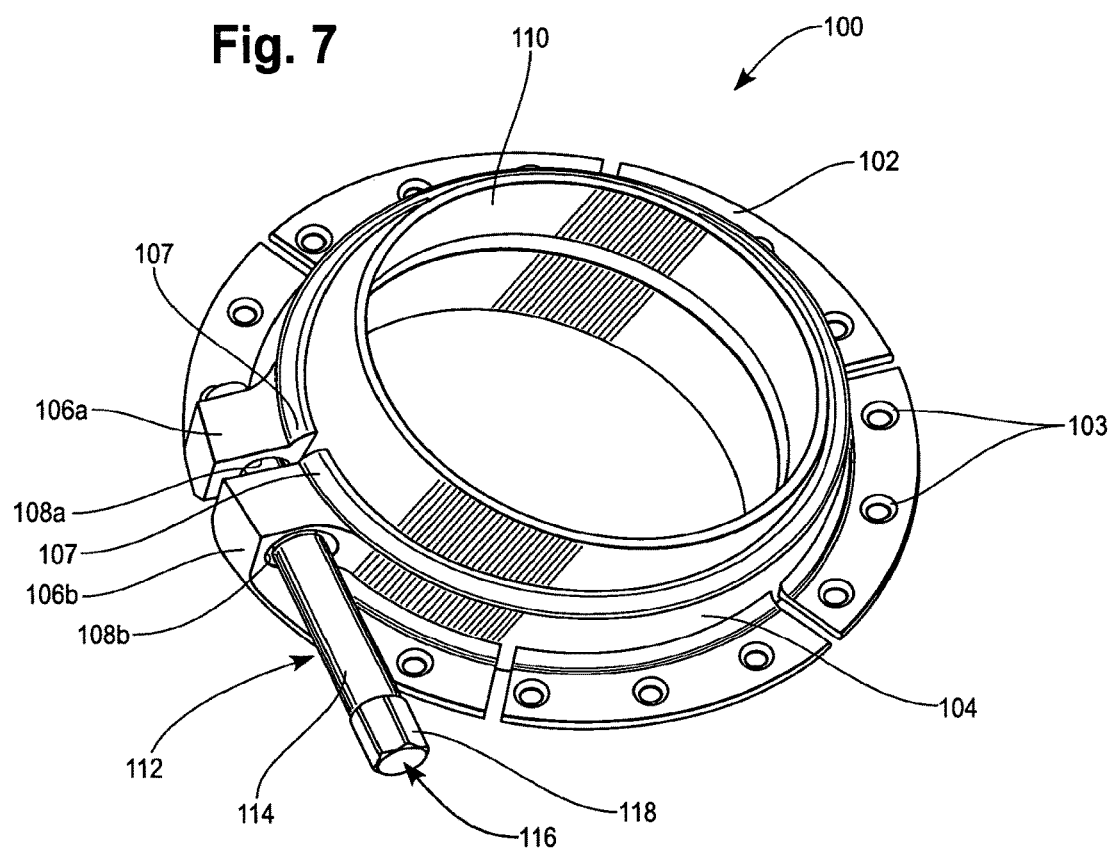
FIG. 7 is a perspective view of another embodiment of the implant connector of the present invention.
Figure 8:
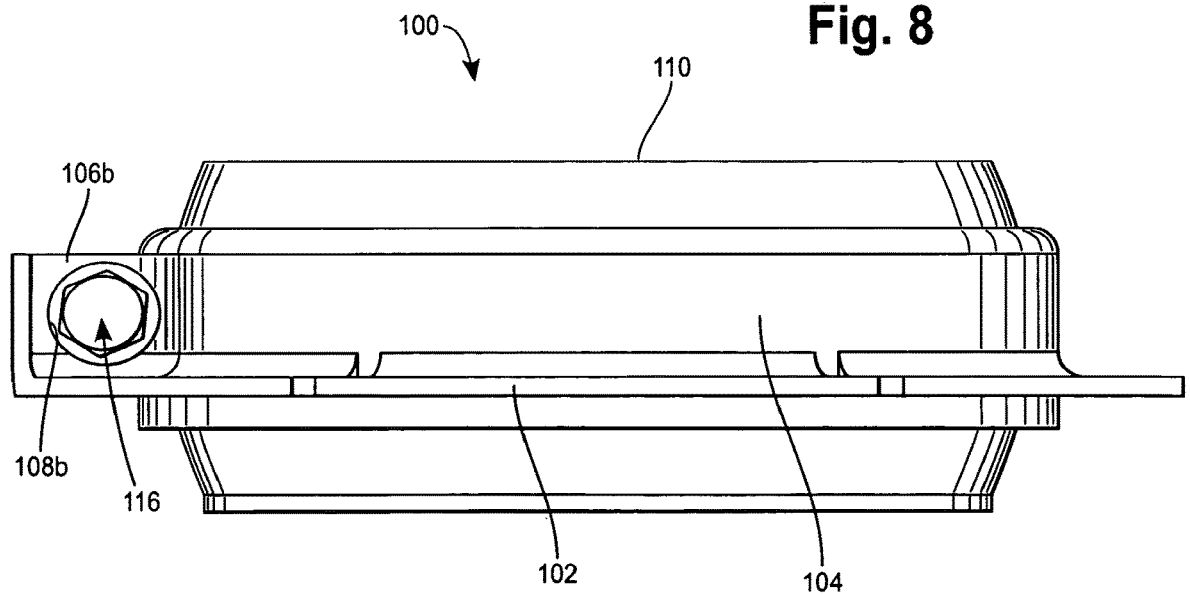
FIG. 8 is a side view of the implant connector of FIG. 7.
Figure 9:
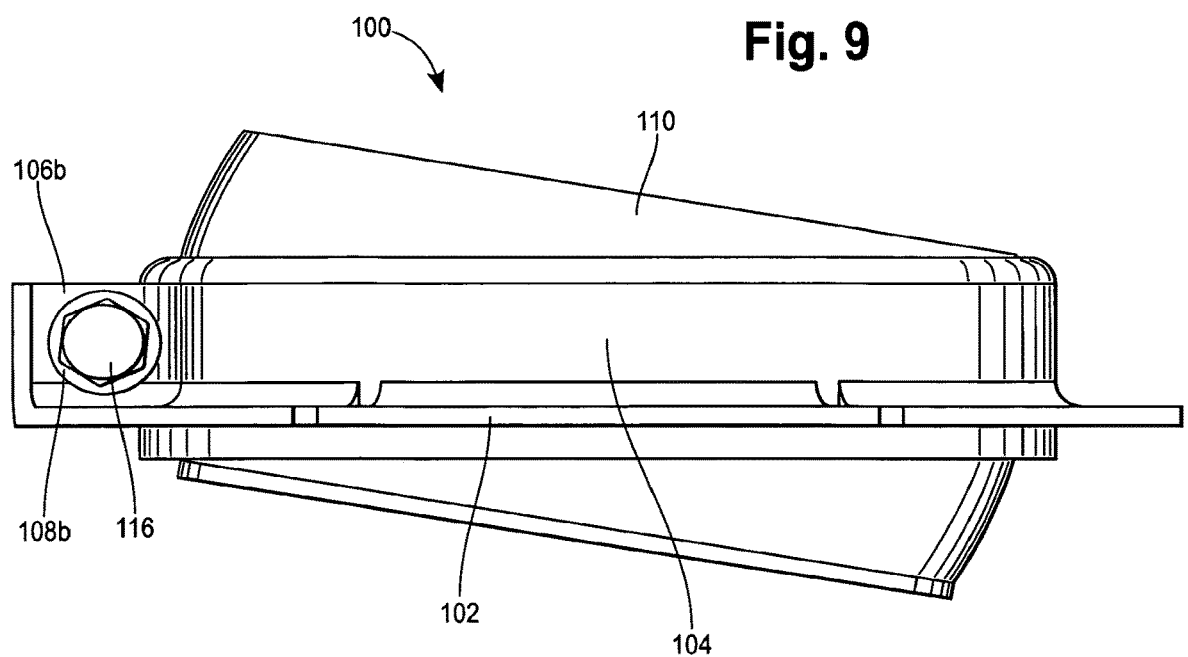
FIG. 9 is a side view of the implant connector of FIG. 7 illustrating the implant adjuster moved to a first position.
Figure 10:
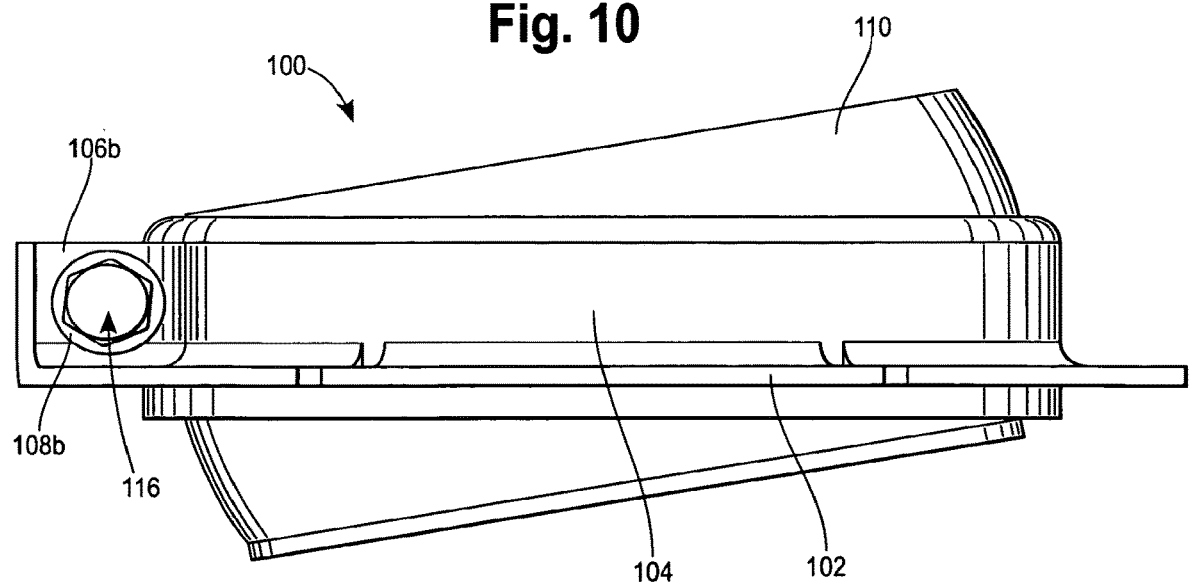
FIG. 10 is a side view of the implant connector of FIG. 7 illustrating the implant adjuster moved to a second different position.

In the illustrated embodiment, the implant connector includes a plurality of flanges 102 integrally formed with a generally vertically extending wall 104 to form a frame of the implant connector. As shown in FIG. 7, each flange 102 defines a plurality of openings or holes 103. The flanges are independent of each other as shown by the spaces between each flange. Although not shown, a first and second ring such as rings 54 and 56 described above are positioned beneath the implant connector 100. At least one suture is secured through one or more of the openings 103, the first and second rings and the heart tissue of a person's body to secure the implant connector 100 to the heart. It should be appreciated that the implant connector 100 may include any suitable number of flanges 102 and each flange may include any suitable number of openings or holes 103. The upwardly extending wall 104 defines a generally circular opening. It should be appreciated that the opening defined by the wall 104 may be any suitable size or shape.

In the illustrated embodiment, the upwardly extending wall 104 has two ends 107. The ends 107 are spaced apart to allow the ends to move towards each other to cause the inside surface of the wall 104 to engage and secure at least a portion of a heart pump to the implant connector. At each of the ends 107, housings or blocks 106a and 106b are integrally formed with the wall 104. Each of the blocks 106a and 106b define corresponding openings 108a and 108b which are constructed to receive an adjustor or screw 112. In this embodiment, the inside surface of housing 106b does not include any threads. The inside surface of block 106a, which defines opening or hole 108a, includes or defines threads which matingly or threadingly engage corresponding threads formed on the screw 112. The screw is inserted through the opening 108b and engage the threads defined by the inside surface of block 106a.

The screw 112 includes a shaft 114 and a head 116 which defines angled or beveled surfaces 118. In operation, a user moves or rotates screw 112 by engaging the angled or beveled surfaces 118 using a suitable wrench or other tool to rotate or turn the shaft 114 of the screw 112. Rotating screw 112 causes the screw to threadingly engage the threads defined by the inside surface of block 106a. As described above, rotating the engaged screw 112 causes the ends 107 of the wall 104 to move towards each other, which causes at least a portion of the inside surface of wall 104 to contact the heart pump and secure the heart pump in the implant connector 100.

In this embodiment, the implant connector 100 includes an implant adjuster, movable member or positioner 110 which is movably connected to the wall 104. The positioner 110 enables a user to move or adjust the position of the heart pump in the heart without having to disconnect or remove the heart pump from the implant connector. The positioner 110 is made of a pliable material such as a rubber material or other suitable polymer material. It should be appreciated that the positioner 110 may be made of any suitable material or combination of materials.

In operation, the implant connector 100 is secured to the tissue of a patient's heart as described above using one or more sutures. Once secured, a heart pump or VAD is inserted through the opening defined by the wall 104. Specifically, the shaft of the hear pump is inserted through the positioner 110 which is positioned adjacent to the inside surface of the wall 104 defining the opening or hole of the positioner. After the shaft of the heart pump is inserted to a desired position or distance in the heart, the adjuster or screw 112 is rotated to move the ends 107 of the wall 104 towards each other and secure or tighten the shaft of the heart pump in place. Once the heart pump is secured in the implant connector, the implant adjuster 110 can be moved or rotated to adjust the positioning of the heart pump with respect to the heart. This enables the optimum or most suitable position for the heart pump to be achieved based on the different configurations of patient's hearts. It should be appreciated that the implant adjuster 110 may be moved to any suitable position or positions.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims, and this application is limited only by the scope of the claims.

The invention is claimed as follows:

1. A method of positioning a heart pump to a cardiovascular system of a person's body, the cardiovascular system including a heart, comprising
    securing a heart pump connector to tissue of the heart, the heart pump connector comprising:
        a frame including first and second arms, the first and second arms defining a frame opening in communication with the cardiovascular system;
        a positioner movably connected to the frame, the positioner defining a proximal opening and a distal opening coaxial with the frame opening in a first position and offset from the frame opening in a second positions, the frame substantially surrounding the positioner when the heart pump is positioned within the cardiovascular system of the person's body;
        a securing member connected to the frame; and
        an adjuster movably connected to the first and second arms, the adjuster is configured to cause the first and second arms to move toward each other and engage the heart pump;
    positioning at least a portion of the heart pump within the frame opening, the proximal opening, and the distal opening;
    moving the positioner and adjusting the position of the heart pump relative to the frame wherein moving the positioner includes rotating and sliding the position relative to the frame and adjusting the heart pump between a first position coaxial with the frame opening and a second position offset to the frame opening;
    adjusting the adjuster to engage the heart pump with the first and second arms to form a seal around the heart pump; and
    when the heart pump is engaged by the first and second arms, moving the positioner to adjust the positioning of the heart pump relative to the heart tissue.

2. The method of claim 1, wherein the heart pump including a shaft, and wherein the method further includes positioning the shaft through the positioner and engaging the first and second arms to the shaft.

3. The method of claim 1, wherein the connector includes an additional securing member positioned between the securing member and the frame.

4. The method of claim 3, wherein the securing member includes a lip substantially covering the additional securing member.

5. The method of claim 3, wherein at least one of the securing members includes one of a felt and a polyester.

6. The method of claim 1, further comprising a sealer removably connected to the frame.

7. The method of claim 6, wherein the sealer includes an o-ring.

8. The method of claim 1, wherein the adjuster is a screw threadingly engaged with at least one from the group consisting of the first and second arms.

9. The method of claim 1, further comprising a pin frictionally connected to at least one from the group consisting of the first and second arms and configured to substantially minimize lateral movement of the adjuster.

10. The method of claim 1, wherein the frame opening is sized to receive at least one suture.

* * * * *